US011602320B2

(12) United States Patent
Regensburger et al.

(10) Patent No.: US 11,602,320 B2
(45) Date of Patent: Mar. 14, 2023

(54) METHOD FOR CREATING A THREE-DIMENSIONAL DIGITAL SUBTRACTION ANGIOGRAPHY IMAGE AND A C-ARM X-RAY DEVICE

(71) Applicant: Siemens Healthcare GmbH, Erlangen (DE)

(72) Inventors: Alois Regensburger, Erlangen (DE); Amilcar Alzaga, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 344 days.

(21) Appl. No.: 16/874,324

(22) Filed: May 14, 2020

(65) Prior Publication Data
US 2020/0375563 A1 Dec. 3, 2020

(30) Foreign Application Priority Data

May 29, 2019 (DE) .......................... 102019207921.0
Oct. 29, 2019 (DE) .......................... 102019216586.9

(51) Int. Cl.
*A61K 49/04* (2006.01)
*A61B 6/00* (2006.01)
(Continued)

(52) U.S. Cl.
CPC ............ *A61B 6/504* (2013.01); *A61B 6/4441* (2013.01); *A61B 6/463* (2013.01); *A61B 6/481* (2013.01);
(Continued)

(58) Field of Classification Search
CPC ......... A61B 6/481; A61B 6/482; A61B 6/504; A61B 6/441; A61B 6/5258; A61B 6/486;
(Continued)

(56) References Cited

U.S. PATENT DOCUMENTS 8,731,262 B2  5/2014  Rauch
9,754,390 B2  9/2017  Heigl
(Continued)

FOREIGN PATENT DOCUMENTS

DE           9216558 U1      3/1994
DE      102012205351 A1     10/2013
(Continued)

OTHER PUBLICATIONS

German Office Action for German Application No. 10 2019 207 921.0 dated Mar. 26, 2020.
(Continued)

*Primary Examiner* — Don K Wong
(74) *Attorney, Agent, or Firm* — Lempia Summerfield Katz LLC

(57) ABSTRACT

The disclosure relates to a method for creating a three-dimensional digital subtraction angiography image of a vascular system of a patient. The method includes: providing a first reconstructed three-dimensional filling image which was acquired during at least partial contrast agent filling of the vascular system with a first contrast agent; providing a second reconstructed three-dimensional filling image which was acquired during at least partial contrast agent filling of the vascular system with a second contrast agent; and subtracting the first three-dimensional filling image from the second three-dimensional filling image so that a three-dimensional subtraction angiography image is produced,
(Continued)

wherein the first contrast agent and the second contrast agent differ in that one of the two causes increased X-ray absorption and the other causes reduced X-ray absorption relative to a vascular system without contrast agent.

16 Claims, 5 Drawing Sheets

(51) Int. Cl.
    *G06T 5/50*     (2006.01)
    *G06T 7/33*     (2017.01)
    *G06T 7/73*     (2017.01)

(52) U.S. Cl.
    CPC .............. *A61B 6/5235* (2013.01); *A61B 6/54* (2013.01); *A61K 49/0438* (2013.01); *G06T 5/50* (2013.01); *G06T 7/33* (2017.01); *G06T 7/73* (2017.01); *G06T 2200/04* (2013.01); *G06T 2207/10116* (2013.01); *G06T 2207/20224* (2013.01); *G06T 2207/30101* (2013.01)

(58) Field of Classification Search
    CPC ..... A61B 6/5235; A61B 6/503; G06T 11/005; G06T 5/50; G06T 2207/20224; G06T 2211/404; G06T 2207/10116; G06T 2207/10081; G06T 2207/30101; G06T 2207/30104; G06T 2207/20221; G06T 17/00

See application file for complete search history.

(56) References Cited

U.S. PATENT DOCUMENTS

| | | |
|---|---|---|
| 2013/0261445 A1 | 10/2013 | Ertel |
| 2015/0126862 A1 | 5/2015 | Pfister |
| 2016/0089095 A1* | 3/2016 | Baumgart ............. G06T 11/008 |
| | | 382/130 |
| 2017/0169553 A1 | 6/2017 | Manhart |
| 2020/0242783 A1 | 7/2020 | Lauritsch |

FOREIGN PATENT DOCUMENTS

| | | |
|---|---|---|
| DE | 102013222674 B3 | 10/2014 |
| DE | 102015224806 A1 | 6/2017 |
| DE | 102019201079 A1 | 7/2020 |
| WO | 9413204 A1 | 6/1994 |

OTHER PUBLICATIONS

Matl, Stefan, et al. "Vascular image registration techniques: a living review." Medical image analysis 35 (2017): 1-17.

Sandoval-Garcia, Carolina, et al. "4D DSA a new technique for arteriovenous malformation evaluation: a feasibility study." Journal of neurointerventional surgery 8.3 (2016): 300-304.

* cited by examiner

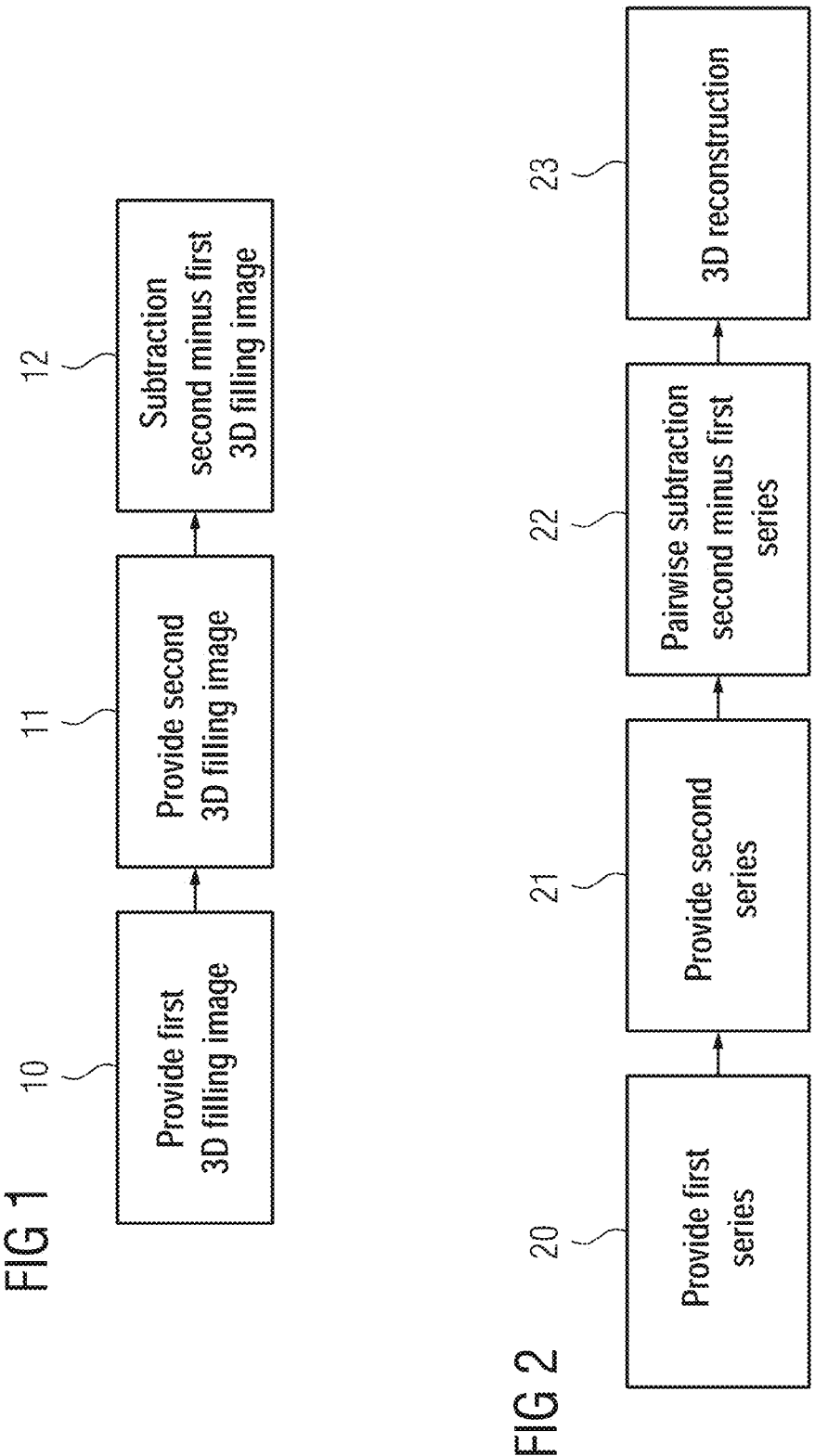

FIG 3
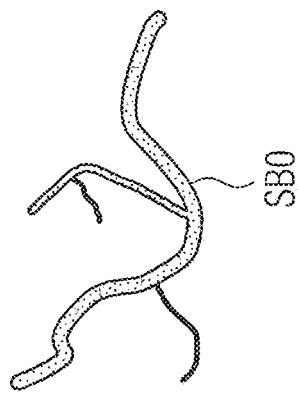
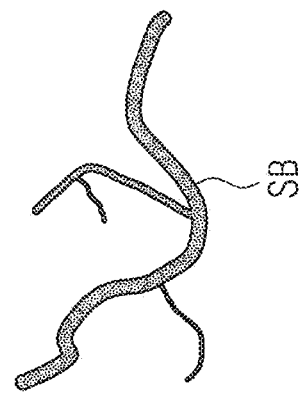
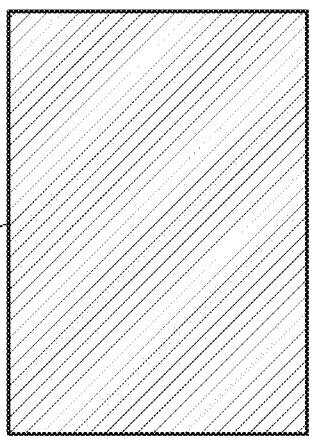
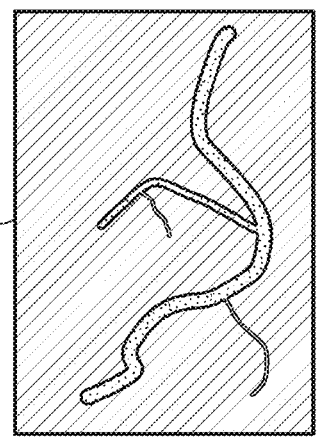
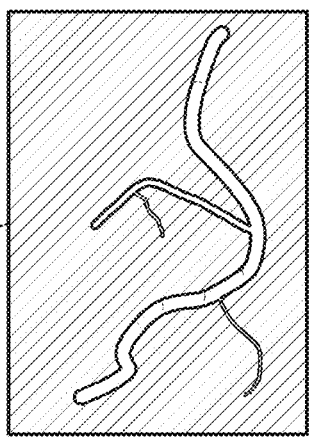
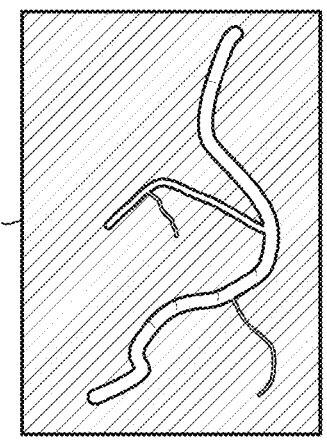
FIG 4

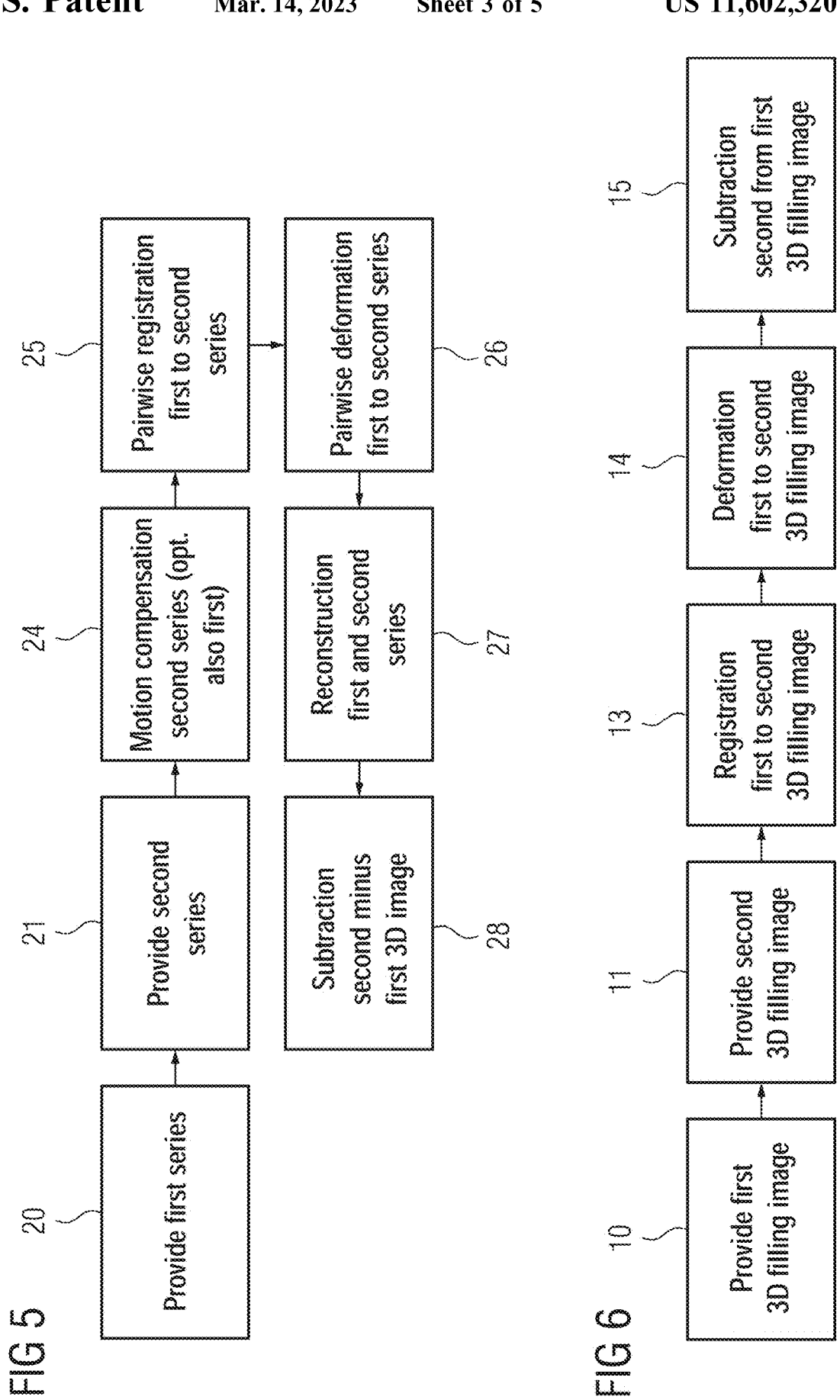

METHOD FOR CREATING A THREE-DIMENSIONAL DIGITAL SUBTRACTION ANGIOGRAPHY IMAGE AND A C-ARM X-RAY DEVICE

The present patent document claims the benefit of German Patent Application No. 10 2019 207 921.0, filed May 29, 2019, and German Patent Application No. 10 2019 216 586.9, filed Oct. 29, 2019, which are hereby incorporated by reference.

TECHNICAL FIELD

The disclosure relates to a method for creating a three-dimensional digital subtraction angiography image of a vascular system of a patient, and to a C-arm X-ray device for carrying out such a method.

BACKGROUND

Digital subtraction angiography (DSA) may be used to examine blood vessels. In the simplest two-dimensional variant, successive (e.g., two-dimensional) projection images of an patient's vascular system are created by an X-ray angiography system (e.g., using a C-arm system), during which a contrast agent (e.g., a substance which causes increased X-ray absorption relative to a vascular system without contrast agent) is injected. This results in a projection image without contrast agent, also referred to as a mask image, and other projection images having contrast agent distribution in the vascular system, the so-called projection filling images. The digital mask image is subtracted from the subsequent projection filling images. This leaves only the parts that differ, e.g., in the vascular system.

Three-dimensional digital subtraction angiography (3D DSA) allows high-resolution representation of, e.g., opacified vascular systems as 3D volumes. For this purpose, a mask run without contrast agent and a filling run with contrast agent may be performed and a series of projection images are created. The two-dimensional projection images may originate from an examination protocol of a C-arm X-ray device rotating around the patient (e.g., DynaCT).

The series of projection mask images may be subtracted from the series of projection filling images and the resulting series of two-dimensional subtraction images are reconstructed into a three-dimensional subtraction angiography image. Three-dimensional DSA images are particularly prone to movements of the patient and deformations of the acquired vascular system, particularly if the movement and/or deformation has taken place between mask run and filling run. The consequence of this may be subtraction artifacts, many small vessels are lost or have poor image quality. Moreover, a comparatively high dose of iodinated contrast agent that may adversely affect renal function is necessary for the filling run.

To avoid disadvantages of conventional three-dimensional DSA, a number of newer methods are known.

Thus, for example, so-called maskless DSA is used in which a mask run is no longer required. However, algorithmic assumptions and/or neural networks may be used here, which run the risk of significantly deviating from reality in the case of unexpected, complex structures.

For motion compensation, two-dimensional/two-dimensional (2D/2D) registration between corresponding projection mask images and projection filling images may be used. However, the disadvantage of this is that vascular systems are not opacified in the mask run, so that registration based on images may only take place based on organ outlines and internal structures that are visible without contrast. In organs such as the liver, which are completely homogeneous in the mask run, the result may be of poor quality.

In order to avoid kidney damage, the alternative use of carbon dioxide ($CO_2$) as a "negative" contrast agent is known (e.g., reduced X-ray absorption relative to a vascular system without contrast agent). However, the image quality using $CO_2$ contrast is significantly lower than using a "positive", e.g., iodinated contrast agent (e.g., increased X-ray absorption of the vascular system relative to a vascular system without contrast agent).

SUMMARY AND DESCRIPTION

The object of the present disclosure is to provide a method which provides high-quality three-dimensional digital subtraction angiography images of a vascular system. The object of the disclosure is also to provide an X-ray device suitable for carrying out the method.

This object is achieved by a method for creating a three-dimensional digital subtraction angiography image of a vascular system of a patient and by an apparatus. The scope of the present disclosure is defined solely by the appended claims and is not affected to any degree by the statements within this summary. The present embodiments may obviate one or more of the drawbacks or limitations in the related art.

The method for creating a three-dimensional digital subtraction angiography image of a vascular system of a patient is provided herein. The method includes providing a first reconstructed three-dimensional filling image acquired during at least partial contrast agent filling of the vascular system with a first contrast agent. The method further includes providing a second reconstructed three-dimensional filling image acquired during at least partial contrast agent filling of the vascular system with a second contrast agent. The method further includes subtracting the first three-dimensional filling image from the second three-dimensional filling image to produce a three-dimensional subtraction angiography image, wherein the first contrast agent and the second contrast agent differ in that one of the two contrast agents produces increased X-ray absorption and the other contrast agent produces reduced X-ray absorption relative to a vascular system without contrast agent.

The disclosure also includes a method for creating a three-dimensional digital subtraction angiography image of a vascular system of a patient. The method includes providing a first series of projection filling images acquired during at least partial contrast agent filling of the vascular system with a first contrast agent. The method further includes providing a second series of projection filling images which was acquired during at least partial contrast agent filling of the vascular system with a second contrast agent. The method further includes subtracting the first series of projection filling images pairwise from the second series of projection filling images to produce a series of subtraction images. The method further includes reconstructing the series of subtraction images into a three-dimensional reconstructed subtraction angiography image, wherein the first contrast agent and the second contrast agent differ in that one of the two contrast agents produces increased X-ray absorption and the other contrast agent produces reduced X-ray absorption relative to a vascular system without contrast agent.

Instead of unopacified, contrast-agent-free projection mask images, the methods therefore use projection filling images from a filling run in which a contrast agent that is the opposite of the "actual" filling run was used. The "positive" contrast agent normally used for a filling run, (e.g., iodinated contrast agent), causes the X-rays to be more strongly absorbed in the region of the vascular system than in the surrounding region. If a "negative" contrast agent, e.g., one containing $CO_2$ (e.g., in the form of microbubbles) is used, the radiation is less strongly absorbed in the region of the vascular system than in the surrounding region. By subtracting the projection images with opposite X-ray absorption, vascular systems may be imaged with much greater contrast compared to known DSA methods. The image quality is enhanced so that significantly improved diagnostics is also possible. Moreover, even vessels or vessel sections of the vascular system may be used in this way for (e.g., 2D/2D or 3D/3D) registration, thereby enabling patient movements to be compensated more easily and with a higher degree of quality. In addition, comparable image quality may be produced using a much lower amount of kidney-damaging "positive" (e.g., iodinated) contrast agent. This protects the patient's health and reduces serious allergic reactions.

According to an embodiment, one contrast agent contains iodine and the other contrast agent contains $CO_2$, e.g., in the form of microbubbles.

According to another embodiment, at least one of the reconstructed three-dimensional filling images is corrected by a motion compensation technique in which movement of the vascular system during acquisition of the series of projection images is compensated, or is used as an already corrected reconstructed three-dimensional filling image. For example, one of the two reconstructed three-dimensional filling images may be defined as "primary", in particular the qualitatively better opacified one, and the other reconstructed three-dimensional filling image as "secondary". Motion compensation may then be performed mainly for the "primary" reconstructed three-dimensional filling image and optionally also for the "secondary" reconstructed three-dimensional filling image. The motion compensation may be carried out, e.g., by a known method according to the prior art, e.g., the method disclosed in German Patent Application No. 10 2019 201 079.2.

The projection filling images of one of the two series of projection filling images are registered pairwise in each case to the projection filling images of the other series of projection filling images by a registration method, wherein this is carried out in particular using orientation points (such as vessel sections or vessel bifurcations) of the vascular system. As the method makes discernible a clear contrast with respect to the surrounding tissue for both series of projection filling images, reliable registration may be carried out on the basis of vascular structures. This is particularly advantageous for organs and in regions of the human body in which no radiovisble structures are present, (e.g., in the liver), as it is here unnecessary to rely on markers or an enlarged image region. For the registration, a known 2D/2D registration technique is used. Such techniques are known, e.g., from the publication by Stefan Matl et al., "Vascular image registration techniques: A living review," Medical Image Analysis 35, 2017, pp. 1-17. As an improvement, the method selected may be adapted to register specifically identical structures, e.g., vessel sections or vessel bifurcations, having opposite contrast opacification with respect to the background or having opposite edges, due to the different contrast agents. Registration on the basis of opposite contrasts is particularly robust and easily carried out.

Here also, one of the two series of projection filling images may be defined as "primary", in particular the qualitatively better opacified one, and the other series of projection filling images as "secondary". The "secondary" series of projection filling images may be registered to the "primary" series of projection filling images. The pairwise registration takes place such that projection filling images of different series are registered with one another, wherein the projection filling images have been acquired in each case at coinciding projection angles of rotation around the patient.

The registration process advantageously produces rigid or deformable registration.

According to another embodiment, the registration process is followed by pairwise deformation or distortion (digital manipulation, e.g., image warping) of regions of the projection filling images of one series relative to the projection filling images of the other series in such a way that the imaged vessels of the vascular system, after deformation, are positioned coincidingly on the projection filling images. In particular, the imaged vessels of the vascular system of the respective projection filling image of one series is digitally manipulated so that they correspond to the shape of the vessels of the corresponding projection filling image of the other series. The image regions between the vessels of the vascular system may also be suitably deformed, e.g., interpolated. The "secondary" series of projection filling images may be deformed in order to be matched to the "primary" series of projection images.

According to another embodiment, at least one series of projection filling images is filtered, (e.g., undergoes a filtering process), or both series of projection images or the series of subtraction images may also be filtered. Such filtering is in the simplest case, e.g., threshold- or spatial-frequency-based.

According to another embodiment, one reconstructed three-dimensional filling image of the two filling images is registered to the other reconstructed three-dimensional filling image (3D/3D-registration), in particular on the basis of orientation points (e.g., vessel sections) of the vascular system. For example, one of the two reconstructed three-dimensional filling images may be defined as "primary", in particular the qualitatively better opacified one, and the other reconstructed three-dimensional filling image as "secondary". Registration is then carried out mainly for the "secondary" reconstructed three-dimensional filling image with respect to the "primary" reconstructed three-dimensional filling image. Reliable registration may also be performed on the basis of vascular structures. Alternatively, other significant vascular structures such as bones or externally applied markers may also be used for registration. As part of registration, in particular a rotation, displacement or deformation field is first produced which is applied to the corresponding reconstructed three-dimensional filling image.

BRIEF DESCRIPTION OF THE DRAWINGS

The disclosure and other advantageous embodiments according to features of the sub-claims will now be explained in greater detail with reference to schematically illustrated examples in the accompanying drawings, but without thereby limiting the disclosure to these examples.

FIG. 1 depicts an example of a sequence of a method.

FIG. 2 depicts another example of a sequence of a method.

FIG. 3 illustrates subtraction of a filling image from a mask image according to the prior art.

FIG. 4 illustrates an example of subtraction of two filling images from one another.

FIG. 5 depicts an example of a sequence of a method including optional acts.

FIG. 6 depicts another example of a sequence of a method including optional acts.

DETAILED DESCRIPTION

FIG. 3 depicts an example of DSA pairwise subtraction of a projection mask image MB and a first projection filling image FB1 according to the prior art, resulting in a known subtraction image SB0 that may only show the vascular system. The projection mask image MB was acquired without contrast agent having been administered, whereas the first projection filling image FB1 was acquired with administration of an in particular iodinated first contrast agent.

As shown in FIG. 4, a fundamental concept of the disclosure is now based on using, instead of a projection mask image, a second projection filling image FB2 that was acquired with administration of a second contrast agent. The second contrast agent differs from the first contrast agent in having an opposite X-ray absorption. Whereas, in the case of the first contrast agent, increased X-ray absorption takes place relative to a vascular system without contrast agent (hereinafter referred to as the "positive" contrast agent because of the X-ray positive effect). In the case of the second contrast agent, reduced X-ray absorption takes place relative to a vascular system without contrast agent (hereinafter referred to as the "negative" contrast agent because of the X-ray negative effect). An example of a positive contrast agent is an iodinated solution. An example of a negative contrast agent is a contrast agent containing $CO_2$ or consisting of $CO_2$, e.g., as a gas or in the form of microbubbles. Subtraction produces a subtraction image SB having a significantly better image quality for a comparable contrast agent concentration. The method is based around applying the subtraction to 3D filling images or series of projection filling images. The two-dimensional projection filling images may be acquired as an examination protocol using a C-arm X-ray device acquisition system rotating around the patient from a large number of projection angles (e.g., DynaCT). A CT scanner may also be used for acquisition.

The opposite contrast opacification of the vessels in the two filling runs may then be used, e.g., for image-based motion compensation using vessels.

Figure 8:
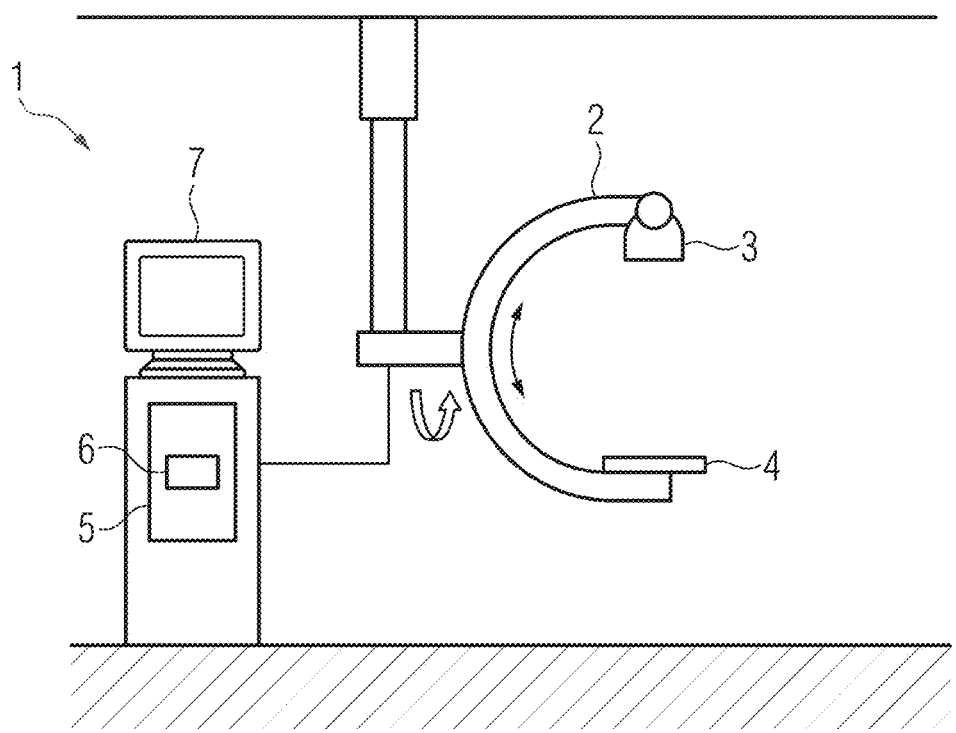
FIG. 8 depicts an example of an apparatus for carrying out the method.

FIGS. 1 and 2 first show the basic acts of the methods. FIG. 1 shows act 10 of providing a first reconstructed three-dimensional filling image acquired during at least partial contrast agent filling of the vascular system with a first contrast agent. In act 11, a second three-dimensional filling image is provided which was acquired during at least partial contrast agent filling of the vascular system with a second contrast agent. The sequence of act 10 and act 11 is not fixed. In act 12, the first three-dimensional filling image is subtracted from the second three-dimensional filling image to produce a three-dimensional subtraction angiography image. Alternatively, this may also be carried out in reverse (second filling image subtracted from first filling image). The first contrast agent and the second contrast agent differ in that one of the two produces increased X-ray absorption and the other reduced X-ray absorption relative to a vascular system without contrast agent. Optional acts prior to act 10 are acquisition of the two series of projection filling images with contrast agent administration (e.g., by a C-arm X-ray device as shown in FIG. 8), reconstruction of the first series of projection filling images to produce the first three-dimensional filling image, and reconstruction of the second series of projection filling images to produce the second three-dimensional filling image.

A second variant of the method is shown in FIG. 2. In act 20, a first series of projection filling images acquired during at least partial contrast agent filling of the vascular system with a first contrast agent is provided, in act 21, a second series of projection filling images acquired during at least partial contrast agent filling of the vascular system with a second contrast agent is provided. Then, in act 22, pairwise subtraction of the first series of projection filling images from the second series of projection filling images (alternatively: of the second series from the first series) takes place so that a series of subtraction images is produced. Pairwise subtraction is to be understood as subtracting corresponding projection filling images that were acquired at the same projection angle (angulation) on the part of the acquisition system. In act 23, the series of subtraction images is reconstructed into a three-dimensional reconstructed subtraction angiography image. The first contrast agent and the second contrast agent differ in that one of the two produces increased X-ray absorption and the other produces reduced X-ray absorption relative to a vascular system without contrast agent. Optional acts prior to act 20 is the acquisition of the two series of projection filling images with contrast agent administration (e.g., by a C-arm X-ray device as shown in FIG. 8).

FIG. 5 shows an exemplary embodiment with additional acts for image-based motion compensation. Optionally, a first series of projection filling images is acquired using a positive contrast agent and a second series of projection filling images is acquired using a negative contrast agent, wherein for this purpose, e.g., so-called DynaCT runs are carried out around the patient. In act 20, the first series of projection filling images acquired during at least partial contrast agent filling of the vascular system with the first contrast agent is provided, in act 21, the second series of projection filling images acquired during at least partial contrast agent filling of the vascular system with the second contrast agent is provided.

In act 24, motion compensation is carried out for one of the two series of projection filling images, in particular the series used as "primary". One of the two series of projection filling images may be defined as "primary", in particular, the better opacified one, and the other series of projection filling images as "secondary". Motion compensation is then carried out primarily for the "primary" series and optionally also for the "secondary" series of projection filling images. The motion compensation may be performed, e.g., using a known prior art method, e.g., as disclosed in German Patent Application No. 10 2019 201 079.2. In this process, the individual projection filling images are transformed as if the series had been motion-free. Optionally, the secondary series is also motion-compensated.

In act 25, pairwise registration of the corresponding projection filling images of the two series to one another is performed. Here, the respective nth projection filling images (e.g., projection filling images acquired from the same projection angle or angulation) of the first series and second series are registered to one another in a deformable or rigid manner on the basis of the positively or negatively opacified vessels. The registration takes place on the basis of vessels or vessel sections of the vascular system (e.g., larger vessels) which are well opacified in both projection images. For example, feature-based registration methods may be used which register readily identifiable vessel bifurcations to one another. The secondary series may be registered to the primary series. In addition, for registration, the opposite contrast opacification, or the opposite edges between the positively and negatively opacified vascular system may be considered in each case.

In act 26, pairwise deformation of the corresponding projection filling images of the two series to one another then takes place. The $n^{th}$ projection of the secondary series is geometrically deformed or distorted ("image warping") in such a way that its (oppositely opacified) vessels of the vascular system have the same positions in the projection filling images as the corresponding vessels of the vascular system in the primary acquisition. The deformation field is suitably interpolated between the vessels. This enables motion and deformations between the two series of projection filling images and within the secondary series to be compensated.

In act 27, the motion-compensated first series of projection filling images and the motion-compensated second series of projection filling images are reconstructed into a first three-dimensional reconstructed filling image and a second three-dimensional reconstructed filling image and, in act 28, subtracted from one another.

FIG. 6 shows an exemplary embodiment with additional acts for motion compensation and distortion of the 3D filling images.

Optionally, a first series of projection filling images with a positive contrast agent and a second series of projection filling images with a negative contrast agent are acquired and reconstructed, wherein for this purpose, e.g., so-called DynaCT runs around the patient are carried out.

In act 10, a first reconstructed three-dimensional filling image is provided which was acquired during at least partial contrast agent filling of the vascular system with a first contrast agent. In act 11, a second reconstructed three-dimensional filling image is provided which was acquired during at least partial contrast agent filling of the vascular system with a second contrast agent. The order of act 10 and act 11 is not fixed. One or both of the three-dimensional filling images may be motion-compensated.

In act 13, the first 3D filling image is registered to the second 3D filling image. In particular, the secondary 3D filling image is again registered to the primary 3D filling image, e.g., on the basis of the locations of vessels or vessel bifurcations of the vascular system. However, organ outlines and other contrast-rich objects may also be used as registration landmarks. The result of the registration is a 3D shift or rotation or a 3D deformation field which are then applied to the secondary 3D filling image in a fourteenth act 14. The objective is that the locations of vessels in the primary and secondary 3D filling image coincide as precisely as possible. In act 15, the second 3D filling image is subtracted from the first 3D filling image (or vice versa).

Figure 7:
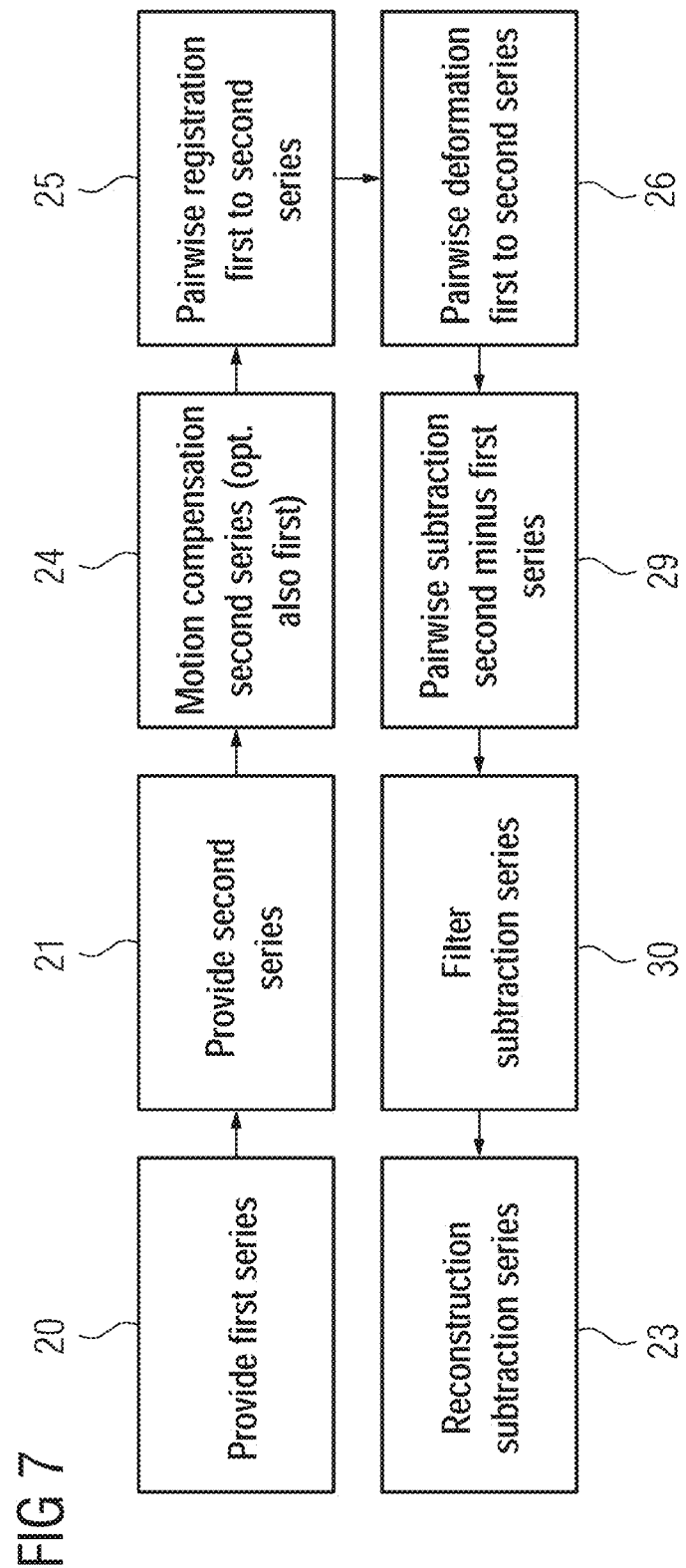
FIG. 7 depicts another example of a sequence of a method including optional acts.

FIG. 7 shows an exemplary embodiment with additional acts for image-based motion compensation similar to FIG. 5, wherein here subtraction takes place prior to reconstruction. After provision of the first series of projection filling images in act 20 and provision of the second series of projection filling images in act 21, motion compensation of one of the two series of projection filling images, (e.g., of the series used as "primary"), is carried out in act 24. The motion compensation is performed primarily for the "primary" series and optionally also for the "secondary" series of projection filling images. In act 25, pairwise registration of the corresponding projection filling images of the two series to one another is carried out. The registration takes place on the basis of vessels or vessel sections of the vascular system (e.g., larger vessels), which are well opacified in the two projection images. The secondary series may be registered to the primary series. In act 26, pairwise deformation or distortion ("image warping") of the corresponding projection filling images of the two series to one another takes place in such a way that their (oppositely opacified) vessels of the vascular system have the same positions in the projection filling images as the corresponding vessels of the vascular system in the primary acquisition. The deformation field is suitably interpolated between the vessels.

In act 29, pairwise subtraction of the first series of projection filling images from the second series of projection filling images (alternatively: of the second series from the first series) then takes place so that a series of subtraction images is produced. Pairwise subtraction is to be understood as subtracting in each case corresponding projection filling images that were acquired at the same projection angle (angulation) on the part of the acquisition system. In act 30, the series of subtraction images is filtered. Here, e.g., "non-vessel structures" may be searched for by image processing in the subtraction result and these structures are completely or partially removed from the subtraction images. "Non-vessel structures" may be image noise, for example. In the simplest case, the filtering may be threshold-based, e.g., image contents below a defined threshold are deleted from the subtraction images or set to zero attenuation. Optionally, spatial filtering or smoothing of the subtracted projection images also takes place. In act 23, the series of subtraction images is then reconstructed into a three-dimensional reconstructed subtraction angiography image.

The examples in FIGS. 5 to 7 describe different approaches for image-based motion compensation on the basis of the opposite vessel contrasts due to the different contrast agents in the two filling runs.

Some of the advantages of the methods for DSA using dual contrast may be the following: For the same image quality of the subtraction result, either less iodinated contrast agent or a lower radiation dose is required. In addition, small vessels into which iodine and $CO_2$ penetrate to differing degrees may be rendered visible in the subtraction, whereas some of these small vessels are not visible if a single contrast agent is used. Moreover, possible inaccuracies in the timing of the contrast agent administration may be balanced out by two filling runs. Alternatively, in the second filling run, a somewhat late timing may be selected compared to the first filling run in order to additionally obtain time information for the contrast agent filling of the vessels—with normal DSA, this is not possible without circuitous methods such as 4D DSA. Subtraction of the series of projection filling images then produces a composite vascular tree in which vessels filled with different contrast agents (e.g., filled only with $CO_2$ and only with iodine) may be differently colored (e.g., on a sign basis or by a suitably selected color scale in the subtraction image).

Additional advantages of DSA using dual contrast and the described motion compensation may include the following.

It is possible to use a first filling run acquired some time before instead of a freshly acquired mask run. The vessel-based registration also enables, e.g., brain shift to be compensated, e.g., a preoperative series of projection filling images with negative contrast by an intraoperative series of projection filling images with positive contrast, for example. In addition, the (e.g., motion-compensated) subtraction of two filling runs with positive and negative contrast also enables a vascular treatment act to be visualized, e.g., if a stenosis was opened or a vessel was selectively embolized. The 3D DSA is particularly suitable for moving and highly deformable organs such as the liver, even with a significant time difference between the two filling runs.

The method is also robust against defective timing, as here there are two possibilities for hitting the correct timing of the contrast agent filling. It is also possible to specifically select for the first filling run a somewhat early timing and for the second filling run a somewhat late timing in order to additionally obtain time information for the contrast agent filling of the vascular system. With known DSA methods, this is only possible via circuitous routes such as 4D DSA. Subtraction then provides a composite vascular tree in which vessels filled only with positive or only with negative contrast agents may be differently colored (e.g., on a sign basis or by a suitably selected color scale in the subtraction image).

An example of a C-arm X-ray device 1 is shown in FIG. 8. Mounted on the C-arm 2 is an X-ray source 3 and a flat-panel X-ray detector 4. The C-arm 2 is configured to rotate around the object under examination and, while doing so, to acquire a series of projection images from different projection directions. Acquisition of this kind with subsequent reconstruction is known, e.g., as cone-beam CT or also DynaCT. The C-arm X-ray device is controlled by a system control unit 5. The C-arm X-ray device also includes a processing unit 6 having at least one processor and software for processing projection filling images of first and second contrast agents, for subtracting projection filling images, for reconstructing projection filling images into a reconstructed three-dimensional filling image, for 2D/2D and/or 3D-3D registration of reconstructed filling images, and for calculating three-dimensional digital subtraction angiographies, wherein the first contrast agent and the second contrast agent differ in that one of the first or second contrast agents causes increased X-ray absorption and the other contrast agent causes reduced X-ray absorption relative to a vascular system without contrast agent. A display unit is provided for displaying the resulting subtraction angiography images and all the other images.

In summary, the disclosure relates, among other things, to a method for creating a three-dimensional digital subtraction angiography image of a vascular system of a patient. The method includes providing a first reconstructed three-dimensional filling image which was acquired during at least partial contrast agent filling of the vascular system with a first contrast agent, providing a second reconstructed three-dimensional filling image which was acquired during at least partial contrast agent filling of the vascular system with a second contrast agent, and subtracting the first three-dimensional filling image from the second three-dimensional filling image so that a three-dimensional subtraction angiography image is produced, wherein the first contrast agent and the second contrast agent differ in that one of the two causes increased X-ray absorption and the other causes reduced X-ray absorption relative to a vascular system without contrast agent.

A similar method is also applicable to 4D-DSA. Here, a 3D image is acquired (e.g., DynaCT or DR) of a vascular tree filled with a first, e.g., negative contrast agent (e.g., $CO_2$), (such as in the brain or liver), while a second, e.g., positive contrast agent (e.g., iodine) flows into the vessels. The change from negative to positive contrast provides additional information for the reconstruction and even allows maskless 4D-DSA. In all the examples, the sequence of the contrast agents may be reversed. This is therefore a method for creating a four-dimensional digital subtraction angiography image sequence of a vascular system of a patient. In the method, a first four-dimensional filling sequence acquired during at least partial contrast agent filling of the vascular system with a first contrast agent and a second four-dimensional filling sequence acquired during at least partial contrast agent filling of the vascular system with a second contrast agent are provided and the first is subtracted from the second filling sequence. The first contrast agent and the second contrast agent differ in that one of the two contrast agents causes increased X-ray absorption and the other contrast agent reduces X-ray absorption relative to a vascular system without contrast agent. For acquisition of the second filling sequence, partial contrast agent filling with both contrast agents may also be provided, for example.

The method for 4D-DSA will now be described in a number of exemplary embodiments.

$1^{st}$ Example

Dual-Contrast Enhanced 4D DSA

A vessel section is reconstructed using projection images in which the vessel section is positively opacified and using projection images in which the vessel section is negatively opacified. The sequence of acts may include the following. In act S0, a mask run is acquired without contrast agent. In act S1, a negative contrast agent is injected, systemically or by a catheter. In act S2, after a delay, a positive contrast agent is injected, systemically or by a catheter (which may be the same as in S1). In act S3, at the instant at which the vascular tree is completely filled with negative contrast agent and the inflow of the positive contrast agent just becomes visible, a filling run with the C-arm is started. For example, a $1^{st}$ projection complete vascular tree is opacified using negative contrast agent, and, in subsequent projections, the positive contrast begins to flow in. In act S5, subtraction and subsequent reconstruction occur.

Compared to "normal" prior art 4D DSA, additional information is available as to the shape of the vessels. A disadvantage of normal 4D DSA is that only a small number of projection images are present for late opacified vessels, which means that these may only be reconstructed in an estimated manner. This may be improved in the case of dual contrast opacification by using projections in which the vessel sections are still negatively opacified. In particular, overlapping of vessels is a problem in 4D DSA which may result in artifacts. The use of earlier projections in which one or both of the mutually obscuring vessels are still negatively opacified enables the vessels to be better separated during reconstruction. In the case of poor timing, in the prior art, many vessels are possibly never filled with contrast agent, and no information of any kind is available for them. In the method proposed, on the other hand, vessel sections that remain negatively opacified right to the end, as the positive bolus no longer reaches them, may nevertheless be reconstructed. Although no information is present, it may be shown in the 4D representation of the inflow or in 3D iFlow in a last frame or collected with a last timestamp.

$2^{nd}$ Example

Acquiring Venous and Arterial Phase Simultaneously (or Effective Doubling of the Acquisition Time of the Inflow Behavior)

In this example, the timing is changed so that different time sections of the hemodynamic flow may be acquired simultaneously. At the start of acquisition, for example, the arterial vascular tree is already filled with negative contrast, and the venous vascular tree begins to fill with negative contrast. On the other hand, in the arterial vascular tree, positive contrast flows in from this time onward. For the reconstruction, the inflow times are then assigned accordingly, e.g., the time shift between negative and positive injection is considered so that a time-consistent inflow image is produced over a time period up to twice the acquisition time. Any time overlaps are averaged accordingly or only one of the two contrast opacifications is used.

This is also possible by simultaneous observation of the in- and outflow of positive contrast agent, but here the transitions are not so sharply defined and for many of the projection images there is again no information about the vessels, as they are not opacified at the time of acquisition.

3$^{rd}$ Example

Direct Reconstruction by "Re-Dying" of the Vessels with Negative Contrast

In the prior art (4D DSA), due to the time inconsistency, there is no simple way of reconstructing the dataset, or rather a large amount of information has to be estimated, e.g., because of the continuity conditions. Particularly for late-filling vessel sections, only a small number of projections are available. The projections of the filling run from the first example are preprocessed as follows. In optional act S10, a subtraction of a mask run without contrast opacification is conducted. In act S11, vessels are identified in the projection images of the filling run or of the subtraction result is conducted, with separate identification of vessel sections having positive and negative contrast opacification, and vessel overlappings and vessel bifurcations are estimated (e.g., on the basis of a learning-based approach). In act S12, digital "re-dying" of the contrast opacification in the projection images is conducted. The negatively opacified light-colored vessels are re-dyed to produce positively opacified vessels (for details see below). In act S13, the re-dyed dataset is reconstructed with completely positive contrast opacification. In optional act S14, iterative re-correction of the re-dying in act S12 is performed, followed by new reconstruction. The criteria include, e.g., consistency conditions of the 3D dataset, vessel connection conditions, detection, and back-projection of artifacts. Optionally, iterative motion correction of the 3D acquisition using vessel-contrast-based methods such as CAVAREC (particularly relevant for the strongly moving liver) is performed. The result of this process is better image quality. In act S15, the inflow response over time is determined, e.g., by projection of the vessel sections segmented in act S11 with positive and negative contrast opacification at the respective times; possibly correction by geometric connection conditions for vessels and consistency of blood flow. In act S16, generation therefrom of 3D datasets with imaged vessels in positive and negative contrast opacification for each point in time, or 3D iFlow representation, is conducted.

Re-dying details include the following. For (almost) every vessel section, there are images with both negative and positive contrast opacification, and it is thereby possible to determine the degree of attenuation of the respective vessel section with positive and negative contrast. A projection that is as overlap-free as possible may be looked for. Alternatively, by global averaging over the negatively and positively opacified vessel sections, it is possible to determine the strength of the opacification of the positive and negative contrast agent (e.g. in Hounsfield units). The grayscale value for the re-dying may also be estimated from the vessel diameter.

4$^{th}$ Example

Maskless 4D DSA

Especially in the neuroradiology area, it may be difficult in the filling run to differentiate the complex bone structures of the skull algorithmically from opacified vessels. Therefore maskless DSA works primarily for 3D DSA, and in this example, using learning-based approaches among other things. The proposed 4D DSA with dual-contrast provides additional information for algorithms which enables opacified vessels and bone to be differentiated: the vessels change their contrast opacification from negative to positive in the course of acquisition.

Alternatively or in addition, learning-based maskless DSA from the prior art may also be applied to reconstruction of the completely positively opacified vascular tree (e.g., act S13) in the 3$^{rd}$ example.

5$^{th}$ Example

Maskless 4D DSA with Simultaneous Biplane 3D Acquisition

For this purpose, a biplane C-arm is required which executes simultaneous 3D acquisition using both planes. The availability of two (virtually) contemporaneous projections from different angulations in each case enables further 3D information about the vessels and their overlap-free contrast opacification to be obtained. In particular, by comparing consecutive projection pairs directly, the 3D location and the time of switching from negative to positive contrast opacification in the respective vessel sections may be determined (and due to the reversal of the contrast opacification, a vessel section may also be definitively identified).

A possible sequence of acts may include the following.

First, greatly diluted iodine contrast agent is injected so that at the start of the acquisition the complete vascular tree is weakly opacified. At this point in time, a second bolus flows into the vessels, with higher iodine concentration, thus producing a change from weaker to stronger positive contrast opacification.

If $CO_2$ in the form of microbubbles was systemically injected, the vessels may not be completely filled with $CO_2$. Here, it is possible to integrate over a plurality of contiguous projections in order to estimate the outlines of the vessel as the envelope of the region in which microbubbles are visible.

6$^{th}$ Example

Using Existing 4D DSA Algorithms

Alternatively, the existing 4D DSA algorithms, configured to detect either only positively or only negatively opacified vessels, may also be applied. This produces a 4D DSA result dataset for the positively opacified vascular tree growing "forwards" in time and a separate 4D DSA result dataset for the negatively opacified vascular tree growing "backwards" in time (e.g., projections are processed in reverse sequence). By comparison between the two result datasets, artifacts may be corrected and consistency conditions improved.

Advantages of 4D DSA include the following.

In one advantage, there is greater robustness of 4D DSA, with fewer artifacts as more information is available. In another advantage, there is the possibility of implementing maskless 4D DSA by using the additional information due to the positive contrast agent. In another advantage, effective doubling of the acquisition time is possible (see, e.g., $2^{nd}$ example). In another advantage, motion compensation using CAVAREC-like approaches by having a completely opacified vascular tree available is possible (e.g., relevant for the liver). In another advantage, no additional contrast agent damage for the kidneys is possible, and $CO_2$ may be broken down without renal exposure.

Although the disclosure has been illustrated and described in greater detail by the exemplary embodiments, the disclosure is not restricted by these exemplary embodiments. Other variations may be derived herefrom by the person skilled in the art, without departing from the scope of protection of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A method for creating a three-dimensional digital subtraction angiography image of a vascular system of a patient, the method comprising:
   providing a first reconstructed three-dimensional filling image that was acquired during at least partial contrast agent filling of the vascular system with a first contrast agent;
   providing a second reconstructed three-dimensional filling image that was acquired during at least partial contrast agent filling of the vascular system with a second contrast agent; and
   subtracting the first reconstructed three-dimensional filling image from the second reconstructed three-dimensional filling image to produce a three-dimensional subtraction angiography image,
   wherein the first contrast agent and the second contrast agent differ in that one of the first or second contrast agents causes increased X-ray absorption and the other contrast agent causes reduced X-ray absorption relative to a vascular system without contrast agent.

2. The method of claim 1, wherein the first or the second reconstructed three-dimensional filling image is corrected by a method for motion compensation in which movement of the vascular system during acquisition of the respective three-dimensional filling image is compensated.

3. The method of claim 1, wherein one reconstructed three-dimensional filling image of the first or second reconstructed three-dimensional filling images is registered to the other reconstructed three-dimensional filling image basis on orientation points of the vascular system.

4. The method of claim 3, wherein the orientation points are vessel sections of the vascular system.

5. The method of claim 3, wherein, as part of the registration, a rotation, a displacement, or a deformation field is first produced which is applied to the corresponding reconstructed three-dimensional filling image.

6. The method of claim 1, wherein the first contrast agent or the second contrast agent is iodinated and contains carbon dioxide.

7. A method for creating a three-dimensional digital subtraction angiography image of a vascular system of a patient, the method comprising:
   providing a first series of projection filling images that were acquired during at least partial contrast agent filling of the vascular system with a first contrast agent;
   providing a second series of projection filling images that were acquired during at least partial contrast agent filling of the vascular system with a second contrast agent;
   subtracting the first series of projection filling images pairwise from the second series of projection filling images to produce a series of subtraction images; and
   reconstructing the series of subtraction images into a three-dimensional reconstructed subtraction angiography image,
   wherein the first contrast agent and the second contrast agent differ in that one of the first or second contrast agents causes increased X-ray absorption and the other contrast agent causes reduced X-ray absorption relative to a vascular system without contrast agent.

8. The method of claim 7, wherein at least one of the reconstructed three-dimensional filling images is corrected by a method for motion compensation in which movement of the vascular system during acquisition of the series of projection filling images is compensated.

9. The method of claim 7, wherein the projection filling images of one of the first or second series of projection filling images are registered pairwise to the projection filling images of the other series of projection filling images in each case by a two-dimensional/two-dimensional registration technique.

10. The method of claim 9, wherein the registration is based on orientation points of the vascular system.

11. The method of claim 10, wherein the orientation points are vessel sections of the vascular system.

12. The method of claim 9, wherein the registration is carried out based on orientation points of the vascular system which are oppositely opacified.

13. The method of claim 9, wherein, following the registration, deformation of the projection filling images of one series relative to the projection filling images of the other series is carried out pairwise such that the vessel sections imaged are positioned congruently on the projection filling images after deformation.

14. The method of claim 7, wherein the series of subtraction images is filtered on a threshold or spatial frequency basis.

15. The method of claim 7, wherein the first or second contrast agent is iodinated and contains carbon dioxide.

16. A C-arm X-ray device comprising:
   an acquisition system comprising:
      a C-arm on which an X-ray source and an X-ray detector are mounted, wherein the C-arm is configured to rotate around an object under examination and to acquire a series of projection filling images from a plurality of projection directions during the rotational movement; and
      a processing unit having at least one processor and software for processing projection filling images of first and second contrast agents, for subtracting projection filling images, for reconstructing projection filling images into a reconstructed three-dimensional filling image, for two-dimensional/two-dimensional and/or three-dimensional/three-dimensional registration of reconstructed filling images, and for calculating three-dimensional digital subtraction angiography images, wherein the first contrast agent and the second contrast agent differ in that one of the first or second contrast agents causes increased X-ray absorption and the other contrast agent causes reduced X-ray absorption relative to a vascular system without contrast agent; and a system controller for controlling the C-arm X-ray device; and a display unit for displaying the subtraction angiography images.

* * * * *